United States Patent [19]

Kang et al.

[11] Patent Number: 5,075,427

[45] Date of Patent: Dec. 24, 1991

[54] POLYMER SURFACE MODIFICATION USING AQUEOUS STABLE DIAZO SOLUTION

[75] Inventors: Uan G. Kang, Ann Arbour, Mich.; Joseph W. Raksis, Columbia, Md.; Clifton L. Kehr, Silver Spring, Md.; Clifford A. Ferrin, Jr., Baltimore, Md.

[73] Assignee: W. R. Grace & Co.-Conn., New York, N.Y.

[21] Appl. No.: 619,846

[22] Filed: Nov. 19, 1990

[51] Int. Cl.$^5$ .................. C07C 245/14; C07C 245/18; C07C 249/14

[52] U.S. Cl. .................................... 534/559; 534/561; 534/560; 525/376; 8/664

[58] Field of Search ............... 525/376; 534/559, 561; 8/664

[56] References Cited

U.S. PATENT DOCUMENTS 3,226,381 12/1965 Breslow et al. ............. 534/561
3,947,247 3/1976 Kohrman et al. ............. 8/664

FOREIGN PATENT DOCUMENTS 0053400 6/1982 European Pat. Off. .

*Primary Examiner*—Shrive Beck
*Assistant Examiner*—Cary A. Veith
*Attorney, Agent, or Firm*—Howard J. Troffkin

[57] ABSTRACT

The present invention is directed to aqueous compositions of organic diazo compounds which are capable of being readily handled in commercial applications and to the surface modification of polymeric substrates utilizing the subject diazo composition.

6 Claims, No Drawings

POLYMER SURFACE MODIFICATION USING AQUEOUS STABLE DIAZO SOLUTION

BACKGROUND OF INVENTION

The present invention relates to aqueous compositions of organic diazo compounds and to a method of modifying the surface of polymers utilizing the subject composition. Specifically, the present invention provides aqueous solutions of organic diazo compounds and to the use of said solutions to modify the chemical nature of the surface of polymeric substrates. The present invention is also directed to aqueous solutions of organic diazo compounds exhibiting storage stability.

The innumerable synthetic polymers which have been prepared, tested and reported in the literature reflect the continuing need to provide materials which have a unique combination of properties. In certain instances polymers have been synthesized in attempts to enhance one or more of their overall or macro properties, such as enhanced tensile strength, inertness to specific environments, porosity and the like. Polymers have been synthesized in attempts to enhance properties required at certain sites of the resultant polymer formation, i.e. surface properties, such as enhanced wettability, adhesion, solvent resistance, herbicidal or pharmaceutical activity and the like. In most instances, the formation of polymers which exhibit enhanced properties at specific sites is not practical or requires costly synthesis. Further, when formed, the newly synthesized polymer has less desirable overall properties than the original non-modified polymer. Thus, the modification of a known synthetic polymer to enhance or modify its properties frequently involves the sacrifice of other desirable properties and, at time, necessitates expensive and complicated procedures and formulations. When surface modification is desired, various methods have been utilized. The surface may be primed with a particular liquid to enhance the treated polymer surface adhesion, wettability or other desired properties. Polyolefins have been subjected to irradiation to enhance their ability to bond to themselves when subjected to heat and pressure in the presence of free radical generating compounds. Other methods of modifying surfaces of preformed polymer articles are well known and include surface degradation, swelling with weak solvents as well as introduction of reactive inorganic groups such as sulfonic, chlorine groups by subjecting the formed polymer article to reactive baths to cause reaction between the polymer article's surface and the reactive moiety. Each of these means of modifying the surface of a polymer article is cumbersome and is limited to a very small range of polymer substrates and modifying reactants. In addition, chemical modification of solid surfaces poses unique problems as compared to chemical reactions in solution or in dispersion. The solid surface is never entirely uniform, and the orientation of molecules at the solid surface is generally restricted, thus limiting their chemical reactivity, and solid surfaces are frequently contaminated with absorbed materials, such as carbon dioxide, water, oxygen, etc., which are frequently very difficult to remove. Atmospheric contamination of a solid surface can present a serious impurity problem in interfacial chemical reactions and can affect the course of the reaction. The reaction kinetics of free radicals in a homogeneous system, e.g. solution, are greatly different from the reaction kinetics of free radicals in a heterogeneous system, e.g. a solid surface.

Since a solid surface differs from a solution in physical, thermodynamic and free energy characteristics, the field of chemical reactions involving solid surfaces has been under recent investigation as a separate and distinct discipline.

U.S. Pat. No. 3,376,278 teaches a means of modifying surface properties of polymers by contacting the surface of the polymer with a diazo compound and irradiating the interface between the diazo compound and the polymer surface with actinic radiation to cause the diazo compound to provide a divalent carbon species with the liberation of nitrogen. The teachings of U.S. Pat. No. 3,376,278 are incorporated herein by reference. The process provided for by this teaching is applicable to a wide variety of polymers and diazo compounds. The major criteria for the polymer is that it contain non-aromatic carbon-hydrogen bonds and for the diazo compound is that the diazo group be attached to a non-aromatic carbon atom. A further discussion of polymers and diazo compounds which can be used is given herein below.

The difficulty with the use of diazo compounds is their high propensity to spontaneously decompose. Such decomposition is normally catastrophic in nature. In order to provide some degree of stability, diazo compounds are normally required to be in the form of a solute in an organic solvent such as toluene, benzene, hexane, methylene chloride and the like but, even here, they require high degrees of dilution and, thus, the presence of high amounts of organic solvent is needed to provide a reasonably stable composition. When diazo compounds have been prepared in aqueous systems, they have been immediately removed from water and made part of an organic solution. It was commonly believed that water and diazo compounds would spontaneously react and, further, that the carbene dissociation product would also react with water to cause deactivation of the specie. The use of diazo compounds as a means of modifying polymeric articles has not found commercial favor because of the hazards normally associated with the diazo compound as well as environmental handling and processing problems associated with the use of large quantities of organic solvents. In addition, the use of organic solvents, in many applications (i.e. modification of food packaging material) requires careful removal of the solvent to avoid contaminating materials which are subsequently put in contact with the modified polymer. The use of organic solvents also presents the problems of contaminating the polymer surface and entrapping residual amounts of reaction by-products. If highly volatile solvents are used, they tend to evaporate, leaving a concentrate of diazo compound which can be hazardous.

It is highly desired and an object of the present invention to provide aqueous compositions in which at least one diazo compound is contained therein. It is further highly desired and an object of the present invention to have the composition substantially free of organic solvent. It is highly desirable and an object of the present invention to provide aqueous storage stable diazo compositions. Finally, it is highly desirable and an object of the present invention to provide aqueous diazo compositions such that the diazo compounds are readily activated to dissociate and react with polymeric substrates to modify them in a safe manner.

SUMMARY OF THE INVENTION

The present invention is directed to aqueous compositions of at least one diazo compound, to storage stable, aqueous diazo compositions and for the use of said compositions to modify the surface of polymeric articles, as fully described hereinbelow. The polymeric surface can be modified by contacting the subject aqueous diazo solution with that portion of the surface for which modification is desired. The modification can be done in a safe and, therefore, commercially acceptable manner as fully described hereinbelow.

DETAILED DESCRIPTION OF THE INVENTION

According to the present invention diazo compounds contained in aqueous solutions have been found to react with polymeric materials to modify the surface chemistry of these materials. Further, it has been found that aqueous solutions of certain diazo compounds can be made storage stable and, yet, be capable of being subsequently activated to form a reactive material for surface modification of polymeric materials.

The subject composition and process can utilize a wide variety of diazo or polydiazo compounds. These compounds are provided by compounds having at least one primary amino group which is bonded to an alpha, non-aromatic carbon atom having a hydrogen atom associated therewith as represented by the following formula:

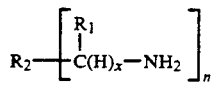
                                                I wherein $R_1$ independently represents an organic group which may be selected from alkyl (i.e. methyl, ethyl, propyl, butyl, pentyl and the like with $C_1$-$C_{10}$ alkyl being preferred and $C_1$-$C_5$ alkyl being most preferred), alkaryl (i.e. benzyl and the like), aryl (i.e. phenyl, naphthyl and the like), cyclic hydrocarbon (i.e. cyclopentyl, cyclohexyl and the like), heterocyclic hydrocarbon (i.e. containing oxygen, nitrogen or sulfur within the ring) or heteroalkyl (i.e. containing at least one ether, secondary or tertiary amino or a sulfide group within the chain). Further, $R_1$ can be selected from active groups which are directly bonded to the alpha, non-aromatic carbon or such active groups can, alternately, be substituted on the organic group described above. The term "active group", as used herein and in the appended claims refers to a chemical group having the activity desired to be imparted to the polymer being modified by the present invention. Such active group can be selected from nitriles, esters of carboxylic acids (preferably a $C_1$-$C_5$ ester group), hydroxyl, alkoxy (i.e. ethers), polyalkoxy (i.e. polyalkyleneoxide), halogen (preferably fluorine or chlorine) as well as complex organic groups (a poly heterocyclic and/or cycloalkyl) such as pharmaceuticals, herbicidal and the like active groups. The group can be chosen based on the activity to be imparted to the polymer surface, the availability of forming or obtaining the above amine compound having said active group and the ability of the amine compound to exhibit solubility in aqueous solutions.

The symbol $R_2$ of the above amine precursor compound represents hydrogen or another monovalent $R_1$ group, as described above, or a polyvalent derivative of the $R_1$ groups described above (e.g. alkylene, alkarylene, arylene, polyvalent cyclic or heterocyclic hydrocarbon, and polyvalent complex organic).

The symbol n is an integer selected from at least 1 with from 1 to 10 being preferred and 1 to 8 being most preferred. Finally, $R_1$ and $R_2$ together can represent a diazole (i.e. pentacyclic hydrocarbon with two nitrogen atoms known as 1,2-pyrazole and 1,3 imidazole) or triazole (a 5 membered hydrocarbon ring having 3 nitrogen atoms therein as, for example 1,2,3-triazole and 1,2,4-triazole) heterocyclic ring with the symbol x is zero while otherwise it represents one. One can alternately view the diazole and triazole ring as providing an alpha hydrogen atom via resonance and thus the symbol x is one (a hydrogen is associated with the alpha carbon) at the point when the amine is converted to the diazo group.

The diazo compounds which results from the precursor compounds of Formula I above are

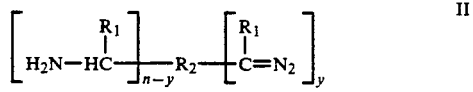
                                                II wherein each of the symbols $R_1$, $R_2$ and n have the same representation as given above and y represents an integer of from at least 1 to the value of n. Thus, at least a portion or all of the primary amino group(s) of compounds I can be converted to diazo groups.

Of the above compounds capable of providing a diazo compound (at least one $-C(H)_x-NH_2$ group converts into $-C=N_2$ and then into a carbene species capable of being processed in aqueous solution, as more fully described below. It has been unexpectedly found that certain diazo compounds can be maintained as storage stable aqueous solutions and subsequently activated to provide the active carbene specie which modifies the surface chemistry of a polymeric material. Such compounds are diazo compounds formed from the above amine wherein $R_1$ represents an electron withdrawing group selected from nitrile, carboxylic acid alkyl or substituted alkyl ester (preferably $C_1$-$C_8$), perhaloalkyl (preferably a perfluoroalkyl), carboxamide (the nitrogen atom being alkyl and/or aryl disubstituted) or a phosphoryl group,

(each R representing aryl or alkyl group); $R_2$ represents hydrogen, unsubstituted or substituted ($C_1$-$C_8$) alkyl or an $R_1$ group; and n is 1 to 10 for Formula I. The substitution of alkyl can be selected from hydroxy, amino, halo, alkoxy, polyalkoxy, aryl, alkaryl or aralkyl.

Examples of such compounds are, for example, nitriles such as diazoacetonitrile, diazomalononitrile, 1-diazo-2-cyanoethane and the like; esters, such as diazo methyl acetate, diazo ethylacetate, diazo methylpropionate and the like; alcohols, such as diazoethanol, diazopropanol, 2-diazopropanediol-1,3 and the like; ethers, such as diazo terminated polyethylene glycol and the like; and complex compounds, such as mono or polydiazo Neomycin, amine terminated polyalkoxides, glucamine, amino derivatives of sugars and the like.

More specifically, diazocompounds which can exhibit stability include, for example, (A) Cyanodiazoalkanes such as $N_2CHC\equiv N$, $N_2C(C\equiv N)_2$ (B) Diazocarbonyl compounds represented by $N_2CHCOOR$ or $N_2C(COOR)_2$ in which R is alkyl [i.e. $-CH_3$, $-CH_2CH_3$], hydroxyalkyl [i.e. $-CH_2CH_2OH$, $-C_6H_{12}OH$, $-CH_2(CHOH)_4CH_2OH$] alkoxy [i.e. $-(CH_2CH_2O)_nCH_2CH_2OH$, etc] or represented by $(N_2CHCOO)_nR$ where n is 2 or 3 and R is a $C_1-C_5$ alkylene, a polyhydroxy alkylene or a polyalkoxy alkylene group.

(C) Fluorodiazoalkanes such as 2-diazo-1,1,1-trifluoropropane; 2-diazoperfluoropropane; 2,2,3,3-tetrafluoro-1-diazopropane; 2,2,3,3,4,4,4-heptafluoro-1-diazobutane and the like.

(D) Diazosphosphoryl Compounds

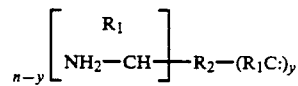

wherein each R represents phenyl, or alkoxy such as $-OCH_3$.

(E) Diazoazoles such as 3-diazo-1,2-diazole; 5-acetamido-4-diazo-1,3-diazole; 5-acetamido-4-diazo-1,2,3-triazole and the like.

Unlike azo compounds, which upon heating produce a free radical, the subject diazo compounds have the ability to be activated to release a molecule of nitrogen and produce a carbene entity. Conventionally, diazo compounds are considered unstable compounds which readily react with water and are easily activated to dissociate in a catastrophic manner. These compounds are, therefore, not retained neat but instead are either stored in very dilute organic solutions under precautionary conditions, or are formed into organic solutions for immediate usage. Such precautions restrict the commercial applications of these diazo compounds to specialized uses.

It has been unexpectedly found that the above described diazo compounds can be formed in aqueous medium and provide a carbene specie under controlled conditions. Thus, when the amino precursor compound of a desired diazo compound of the above formula is dissolved in water, the resultant aqueous solution can be readily used directly to provide a carbene specie which is capable of modifying the surface of a polymer substrate. This is accomplished by contacting the aqueous amine solution with the polymer substrate in the presence of an alkali metal or alkaline earth metal nitrite salt under acidic conditions. The exact order of introducing the precursor amine solution, acid and nitrite salt is not critical. It is preferable to first contact the polymer substrate with the aqueous amine solution and then to introduce the nitrite salt. The amine solution may be acidified (pH of about 2-5 preferably 3-4) prior to contact with the polymer or prior to or subsequent to introduction of the nitrite salt.

The polymer is contacted with the acidified aqueous solution at temperatures of from about $-5°$ C. to about 50° C. and preferably from about 10° C. to 30° C. Ambient temperature and pressure are most suitable. The polymer and the acidified aqueous solution are allowed to remain in contact for a time such that sufficient carbene formation and reaction occurs. This normally is from about 1 minute to about 200 minutes. The exact time will depend on the particular diazo compound as well as the temperature of contact. The amine precursor, and thereby the diazo compound, can be present in the solution in concentrations ranging from 1 to 20 weight percent, preferably from 1-10 weight percent of the solution.

The polymer substrate is thus modified by the carbene specie

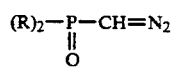

for Formula I where y is at least 1 but not greater than n under controlled conditions in an aqueous, non-explosive environment. The aqueous residual solution can be easily removed and disposed of and does not provide a safety or environmental hazard.

It has also been unexpectedly found that certain diazo compounds as described above can be formed into storage stable aqueous solutions of formed diazo compound. It has been found that these diazo compounds can be formed into compositions which exhibit enhanced storage stability while being readily activated under controlled conditions to provide desired carbene species which are capable of modifying polymeric surfaces. The composition is composed of an aqueous solution of at least one diazo compound having at least one electron withdrawing group bonded to an alpha, non-aromatic carbon atom in combination with a stabilizing agent. The term "stabilizing agent," as used herein and in the appended claims, refers to compounds which are water soluble, inert to the diazo compound and capable of causing and maintaining the aqueous diazo solution at a pH of between 6.5 and 7.5 and more preferably between 6.7 and 7.3 and most preferably from 6.9 to 7.1. The stabilizing agent may be an acidic agent, such as an inorganic or organic acid as, for example, hydrochloric, sulfuric acid, nitric acid, acetic acid, propionic acid and the like. If the initial solution is acidic, the solution can be caused to achieve the required pH by use of a base such as an alkali metal or alkaline earth metal oxide or hydroxide and the like. In addition, the stabilizing agent may be a salt capable of causing the solution to achieve and maintain the required pH. Known salts include phosphates (i.e. $KH_2PO_4$, $Na_2HPO_4$, their mixtures and the like), alkali or alkaline earth bicarbonate, ammonium bicarbonate and the like. The stabilizing agent useful for any particular solution will depend upon the identity of the $R_1$ and $R_2$ groups of the diazo compound. The particular stabilizing agent and the amount needed can be readily determined by minimum conventional experimentation.

The above-described stable, aqueous composition, comprising an aqueous solution of one or a mixture of the above-identified diazo compounds (preferably one) having electron withdrawing group(s) directly attached to the diazo carbon atom and a stabilizing agent, has been found to be storage stable over a sustained period. The solution should be maintained at 25° C. or less (i.e. from $-10°$ to $+25°$ C.) and preferable at a temperature of 20° C. or less (i.e. from $-10°$ C. to $+20°$ C.) with the most preferred temperature being from $-10°$ to $+10°$ C. The solution has been found to be readily handled and safe over periods extending to 6 months and greater when maintained at the preferred temperature range.

The stable aqueous solution of diazo compound having electron withdrawing group(s), as described above, can be present in the aqueous solution in amounts of up to about 75 weight percent although lower amounts are preferred. Such solutions are stable to impact and can be readily handled without hazardous explosive reaction. It is preferred to have the aqueous solution contain the diazo compound in concentration of from about 5 to 50 weight percent. Solutions which have high concentrations of greater than about 10 weight percent are suitable for storage but should be diluted at the time of application to polymer surface so that upon activation, the resultant carbene species reacts with the polymer substrate in a controlled manner.

Storage stable compositions of the described diazo compounds can be readily formed by dissolving the corresponding organic amine precursor into aqueous solvent and treating the amine with an alkali metal nitrite (at least molar equivalence to the amine) and with sufficient inorganic acid (i.e. sulfuric acid, hydrochloric acid) to provide the active diazotizing agent, $HNO_2$. The reaction is conventionally carried out at a pH of about 3.5 to 4.0. Instead of the conventional procedure of rapidly extracting the formed diazo compound with an organic solvent, such as methylene chloride, the aqueous solution in which the diazo compound is formed can be readily converted into the present storage stable composition by the direct addition of a stabilizing agent, as described above. Thus, the storage stable, yet reactive, composition can be readily formed without the need for organic solvents nor extra steps such as extraction as required by prior known techniques.

It has unexpectedly been found that the present stable aqueous composition can be activated and directly used as an active source of carbene species. It has been found that the subject composition can be activated by introducing catalytic amounts of a water soluble transition metal salt, preferably copper, rhodium or lead salts into the aqueous composition. Such salts include, for example, copper nitrate, copper sulfate, copper acetate, rhodium acetate, rhodium perfluoroacetate, lead acetate and the like. The amount of such salt should be only a catalytic amount ranging from about 0.005 to 0.075 weight percent based on the concentration of diazo compound present, with the preferred amount being from 0.01 to 0.06 weight percent. Increasing the concentration of the catalyst will increase the rate of dissociation of the diazo compound. Thus the specific amount of catalyst required will depend upon the concentration of the diazo compound in the composition, the amount of time required to apply the activated solution to the polymer surface as well as the temperature of the activated solution. The amount of catalyst required for any particular activation can be readily determined and custom designed for a particular application.

The activated aqueous composition can be readily applied to the polymeric surface and allowed to remain thereon to supply carbene species and permit their contact with the polymer surface. Normally, the diazo compound commences dissociation within a period of about 1 to 30 minutes after activation. The time can be accelerated by increasing the concentration of catalyst in the diazo solution. An alternate manner of accelerating the dissociation time is to subject the interface between the applied activated aqueous solution and the polymer to heat (normally 40°–80° C. and, preferably, between 40°–60° C.) or with actinic irradiation such as supplied by a UV radiation source.

Thus, the above-described diazo aqueous solution can be retained and stored as a stable entity for sustained periods. The solution (or desired portion thereof) can be readily activated to serve as a suitable source of carbene species to thus modify polymeric surfaces. The amount of catalyst alone or a combination of catalyst and supplemental activating means (heat or actinic energy) can be customized to provide the carbene species at the appropriate time in the processing of the polymer. The activating catalyst and supplemental activation can be done simultaneously or as different stages (i.e. first treat catalyst in very small dosages to give extended work time, apply the activated solution to the polymer surface and finally, treat the surface/solution interface with heat and/or actinic energy to further promote activation and accelerate dissociation).

A wide variety of organic amines can be converted into the corresponding diazo compound, storage stable or not, as the case may be. The amine precursor is selected to provide the desired active group for the particular modification of the surface of the polymeric product. The amine precursors must be soluble in aqueous solutions to a degree sufficient to permit their conversion into the corresponding diazo compound, as described above. It has been found that the above described aqueous solution can be readily used directly to modify the chemical identity of a polymer surface or, as also described above with respect to certain diazo compounds, can be readily formed into the subject storage stable composition by providing the solution with the required stabilizing agent. In both instances, the resultant composition has been found safe to handle and not subject to catastrophic decomposition, as exhibited by presently known compositions. Further, the storage stable diazo solutions can be activated and used to modify the surface chemistry of polymeric substances in a safe and commercially feasible manner.

It is known that the solid surfaces of polymers which contain a plurality of non-aromatic carbon-hydrogen bonds can be modified by reacting with a divalent carbon species, such as provided by the dissociation of a diazo compound. Although not meant to be a limitation on the subject invention, the reaction can be viewed as either an insertion or hydrogen abstraction mechanism or carbenium ion substitution. Polymers which contain non-aromatic (i.e. aliphatic, heterocyclic and alicyclic) carbon-hydrogen bonds within the polymer structure are well known. For the purpose of this invention, the most useful polymers are those in which the carbon atoms of the carbon-hydrogen bonds do not constitute a part of an aromatic ring system and in which at least 50 percent of the non-aromatic carbon atoms of the polymer contain at least one such carbon-hydrogen bond. Saturated or unsaturated aliphatic homopolymers or interpolymers, including aliphatic, cycloaliphatic and mixed aromatic-aliphatic polymers are the most preferred, as exemplified by polyvinyl chloride, casein, polyvinylidene chloride, polypropylene, polyethylene, polymethyl siloxane, polystyrene, vinyl chloride-vinylidene fluoride copolymer, natural rubber, styrene-acrylic acid copolymer, gelatin, cellulose acetate, polyacetal, polyethylene terephthalate, cellophane, ethylene-propylene copolymers, polyvinyl fluoride, polyvinyl chloride, polyvinyl alcohol, polyvinyl ethers, acrylate and methacrylate polymers and copolymers, polybutadiene, etc. In addition to the reaction of the divalent carbon species with the carbon-hydrogen bonds, the presence of unsaturated linkages, hydroxyl, amine, ether groups and the like, in the polymer also provides sites which can be attacked by the divalent carbon species as is known.

A further benefit of the use of the subject aqueous system, over the organic solutions of the prior art, is the ease of removal of excess and exhausted solution from the polymer surface without contaminating the surface with organic residue. The present process permits washing the surface of the polymer with water to remove spent solution. In view of the fact that most organic polymers are not soluble in or even plasticized by water, the water is an inert material easily removed from the polymer surface without leaving residual material.

The resultant polymer with its surface containing the new organic species, as provided herein, show enhanced desired properties such as adhesion, wettability, solvent resistance, enhanced adherence of inks or dyes bioactivity, drug delivery and the like. The amount of the organic species required on the polymer surface does not have to be high. Normally, surface concentrations (as shown by ESCA or other similar analytical techniques) need only be in the range of about 1 to 10% (preferred about 2-8%) to provide the desired modified properties. Even lower percentages have been found to modify the surface of polymers although exact amounts are difficult to determine because of analytical techniques. Higher concentrations can also be used but are generally not economical as desired properties are achieved within the above described ranges.

The following examples are given for illustrative purposes only and are not meant to be a limitation on the invention as defined by the claims appended hereto. All parts and percentages are by weight unless otherwise indicated.

EXAMPLE I

Aminoacetonitrile (100 parts) was dissolved in 540 parts water and then cooled with an ice bath to about 5° C. 90 parts sodium nitrite were added to the solution which was then adjusted to pH 4 with ice cold 25% conc. $H_2SO_4$. The solution was mixed for about 30 minutes to insure complete conversion to the diazo compound. The solution was neutralized to pH 7.0 with approximately 20 ml of 5% sodium carbonate and the pH was monitored. Small amounts of additional sodium carbonate were added periodically over the initial period (3 hours) until the pH stabilized.

The stabilized diazo composition was stored at 5° C. over a period of 6 months. Samples were taken periodically and tested for diazo activity by extracting the diazo compound from the solution with methylene chloride and analyzing with IR nitrile absorption at 2210 $cm^{-1}$ and diazo absorption at 2100 $cm^{-1}$ and for stability by subjecting the samples to an impact test. All of the samples were found to have the diazo compound present but were stable to an impact test of placing a 0.5 ml sample between two stainless steel sheets and subjecting it to an impact force of about 5 ft. lbs. Unstabilized samples exploded when subjected to this test.

EXAMPLE II

A bag of low density polyethylene having dimensions of 10 cm wide and 10 cm long was filled with 10 ml of the composition of Example I which was activated by adding about 0.1 ml of 5% solution of cupric acetate. The activated solution was allowed to remain on the bag's inside surface for approximately 10 minutes. The surface was then washed with water and dried at 40° C. under vacuum. The surface tension was measured using a commercially available Surface Tension Kit (from Sherman Treaters) which compares surface tension of known standards to present material. It was observed that the surface tension of the presently treated sheet increased from 33 dynes/cm (untreated) to greater than 55 dynes/cm (treated) which indicated a dramatic increase in the sheet's surface ability to be wetted by liquids, inks, etc. (The Surface Tension Kit provides values up to 55 dynes/cm.) The sample was also analyzed using conventional standard techniques of surface infrared spectroscopy and exhibited nitrile peak at 2210 $cm^{-1}$ and by ESCA (Electron Spectroscopy for Chemical Analysis) and showed the presence of nitrogen atoms on the polymer sheet surface.

EXAMPLE III

A sheet formed from ultra high molecular weight polyethylene (MW=2,000,000) was subjected to surface modification according to the same procedure described in Example II above. The treated sheet was analyzed by surface IR and ESCA and showed the presence of nitrile and nitrogen atoms on the polymer surface. The surface tension of the modified sheet was measured and found to be greater than 55 dynes/cm and compared to its unmodified original value of 33 dyne/cm. The modified sheet was subjected to a bath of 35% $H_2SO_4$ at 80° C. for 3 days and retested. No changes were observed.

EXAMPLE IV

The procedure of Example II was repeated except that the solution/sheet interface was subjected to UV radiation (Source: Ferro Lamp) for two minutes.

The resultant product provided the same analytical results as attained from the product of Example II.

EXAMPLE V

To exhibit an in situ formation and application of modification of polymer surface using aqueous diazo compounds, 10 parts of amine terminated polyethylene oxide (MW=500) was dissolved in 50 parts of water and cooled to 5° C. 6.5 parts of sodium nitrite was added to the solution.

Polysulfone films were subjected to the above solutions and then the pH was adjusted down to 4 with ice-cold 25% $H_2SO_4$. The films were removed from the solution after about 200 minutes, washed with water and then dried at 40° C. under vacuum for 30 minutes. The treated films exhibited surface tension of greater than 55 dynes/cm while untreated samples showed only 51 dynes/cm. The treated samples exhibited improved hydrophilic properties and high surface tension and retained these properties even after being subjected to: 30 minutes of sonication at 50° C.; 10 days in a NaOH solution at pH 13 and 80° C.; and 3 days in a $H_2SO_4$ solution at pH 1 and 80° C.

EXAMPLE VI

An aqueous solution of diazoethanol was formed from 3.05 parts ethanolamine treated with 4.14 parts $NaNO_2$ in 50 parts water at 0°-5° C.

Polysulfone films were immersed in the above solution which was activated by adjusting the pH to 4 with ice cold 25% $H_2SO_4$. The surface tension increased from 51 dynes/cm to 54 dynes/cm after 30 minutes of contact and to greater than 55 dynes/cm after 3 hours of exposure.

EXAMPLE VII 10 parts of Neomycin sulfate was dissolved in 100 parts water. 3.36 parts sodium nitrite was added while mixing the solution with a magnetic stirrer and then the solution was adjusted to a pH of 4 with ice cold 25% sulfuric acid at 0°–5° C. The solution was continued to be mixed for about 30 minutes.

Five 1"×3" polysulfone films were submerged in the solution at 0° for 90 minutes and then heated to ambient temperature and maintained for 30 minutes. The film was then removed from the solution, washed with water and methanol and dried at 40° C. for 30 minutes under vac.

The treated films were analyzed and were shown to have the Neomycin group bonded to the surface of the polymer. Surface tension increased from 51 dynes/cm (untreated polymer as control) to greater than 55 dynes/cm. Polymer films treated with Neomycin sulfate aqueous solutions which were not acidified continued to show surface tension of 51 dynes/cm.

EXAMPLE VIII

The procedure of Example VII was repeated except that the polysulfone membranes (PM-10, Amicon) were submerged in the diazo-Neomycin solution in an Erlenmyer flask on an orbital shaker and tested for percent water flux recovery after bovine syrum albumin (Upjohn Co.) exposure.

40 parts of Neomycin sulfate was dissolved in 400 g. water and 28 parts of sodium nitrite was dissolved in 200 parts of $H_2O$. Both solutions were cooled in an ice salt bath to 0° C.

100 ml of the cooled Neomycin sulfate solution and 50 ml of the cooled sodium nitrite solution were mixed in 250 ml wide-mouth Erlenmyer flask. A polysulfone microporous sheet (Amicon PM-10 membrane) was submerged in the solution and then the pH of the solution was adjusted to 4.0 by dripping ice cold 25% $H_2SO_4$ into the flask. The flask was maintained at 25° C. with agitation in a water bath for 1 hour.

The treated membrane was washed with 5 portions of 30 ml deionized water and then mounted as the filtering membrane in a stirred ultrafiltration stirred cell (Amicon 8050). 20 ml of Bovine Syrum Albumin (BSA) (1 mg/ml in 0.1M $NaH_2PO_4$ at pH 7) was fluxed through the cell. The membrane was then rinsed with 30 ml of deionized water for 5 minutes to remove residual BSA. 50 ml of deionized water was introduced into the cell and fluxed for 30 sec. at 30 psi to exhibit a 57% water flux recovery after fouling and cleaning compared to a 34% water flux recovery for untreated membrane. This result shows that the diazo-Neomycin treated membrane exhibits enhanced biocompatability.

What is claimed:

1. A storage stable diazo composition consisting essentially of an aqueous solution having a temperature of less than 25° C. containing at least one diazo compound represented by the formula:

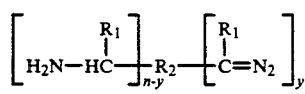

wherein $R_1$ represents an electron withdrawing group, $R_2$ represents a monovalent (when n is 1) group selected from an $R_1$ group, an unsubstituted or substituted alkyl or hydrogen or a polyvalent (when n is greater than 1) group selected from alkylene, alkarylene, aralkylene, arylene, polyvalent cyclic hydrocarbon or polyvalent heterocyclic hydrocarbon, n is an integer of at least 1 and y is an integer of from at least 1 to n and a stabilizing agent present in an amount sufficient to cause and maintain the solution at a pH of from 6.5 to 7.5 and maintain the diazo compound therein over a sustained period of time.

2. The composition of claim 1 wherein the electron withdrawing group is selected from nitrile, carboxylic acid ester, perhaloalkyl, carboxamide or phosphoryl group.

3. The composition of claim 2 in which the solution is maintained at a pH of from 6.7 to 7.3.

4. The composition of claim 2 wherein the stabilizing agent is selected from an alkali or alkaline earth metal oxide or hydroxide or mixtures thereof.

5. The composition of claim 2 wherein the stabilizing agent is selected from an inorganic phosphate or mixture thereof.

6. The composition of claim 2 wherein the electron withdrawing group is a cyano group.

* * * * *